US011534229B2

(12) United States Patent
Jarrard

(10) Patent No.: US 11,534,229 B2
(45) Date of Patent: *Dec. 27, 2022

(54) SYSTEM AND METHOD FOR CONTROLLING POWER BASED ON IMPEDANCE DETECTION, SUCH AS CONTROLLING POWER TO TISSUE TREATMENT DEVICES

(71) Applicant: Boston Scientific Scimed, Inc., Maple Grove, MN (US)

(72) Inventor: Jerry Jarrard, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 220 days.

This patent is subject to a terminal disclaimer.

(21) Appl. No.: 16/364,518

(22) Filed: Mar. 26, 2019

(65) Prior Publication Data
US 2019/0216527 A1   Jul. 18, 2019

Related U.S. Application Data

(63) Continuation of application No. 14/799,346, filed on Jul. 14, 2015, now Pat. No. 10,278,765, which is a
(Continued)

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1206* (2013.01); *A61B 18/14* (2013.01);
(Continued)

(58) Field of Classification Search
CPC . A61B 18/1233; A61B 18/1206; A61B 18/14; A61B 18/1492; A61N 1/32; A61N 1/36128
See application file for complete search history.

(56) References Cited

U.S. PATENT DOCUMENTS

| 4,739,759 A | 4/1988 | Rexroth et al. |
| 4,907,589 A | 3/1990 | Cosman |

(Continued)

FOREIGN PATENT DOCUMENTS

| EP | 908713 A1 | 4/1999 |
| JP | 59167707 A2 | 9/1984 |

(Continued)

OTHER PUBLICATIONS

Cantwell C. P., et al., "MRI MRI Features after Radiofrequency Ablation of Osteoid Osteoma with Cooled Probes and Impedance-Control Energy Delivery," American Journal of Roentgenology, 2006, vol. 186 (5), pp. 1220-1227.

(Continued)

*Primary Examiner* — Jennifer Pitrak McDonald
*Assistant Examiner* — Pamela M. Bays
(74) *Attorney, Agent, or Firm* — Bookoff McAndrews, PLLC

(57) ABSTRACT

A system and method of controlling the application of energy to tissue using measurements of impedance are described. The impedance, correlated to the temperature, may be set at a desired level, such as a percentage of initial impedance. The set impedance may be a function of the initial impedance, the size and spacing of the electrodes, the size of a targeted passageway, and so on. The set impedance may then be entered into a PID algorithm or other control loop algorithm in order to extract a power to be applied to a treatment device.

13 Claims, 7 Drawing Sheets

Related U.S. Application Data continuation of application No. 12/179,301, filed on Jul. 24, 2008, now Pat. No. 9,108,052.

(60) Provisional application No. 60/951,655, filed on Jul. 24, 2007.

(51) Int. Cl.
*A61N 1/36* (2006.01)
*A61N 1/32* (2006.01)
*A61B 18/00* (2006.01)

(52) U.S. Cl.
CPC ............ *A61B 18/1492* (2013.01); *A61N 1/32* (2013.01); *A61N 1/36128* (2013.01); *A61B 2018/00214* (2013.01); *A61B 2018/00267* (2013.01); *A61B 2018/00541* (2013.01); *A61B 2018/00577* (2013.01); *A61B 2018/00595* (2013.01); *A61B 2018/00642* (2013.01); *A61B 2018/00702* (2013.01); *A61B 2018/00791* (2013.01); *A61B 2018/00875* (2013.01); *A61B 2018/00898* (2013.01); *A61N 1/36146* (2013.01)

(56) References Cited

U.S. PATENT DOCUMENTS

| | | | |
|---|---|---|---|
| 5,425,023 A | 6/1995 | Haraguchi et al. | |
| 5,496,312 A | 3/1996 | Klicek | |
| 5,540,681 A | 7/1996 | Strul et al. | |
| 5,562,721 A | 10/1996 | Marchlinski et al. | |
| 5,688,267 A | 11/1997 | Panescu et al. | |
| 5,702,386 A | 12/1997 | Stern et al. | |
| 5,735,846 A | 4/1998 | Panescu et al. | |
| 5,743,903 A | 4/1998 | Stern et al. | |
| 5,782,827 A | 7/1998 | Gough et al. | |
| 5,837,001 A | 11/1998 | Mackey | |
| 5,931,835 A | 8/1999 | Mackey | |
| 5,957,961 A | 9/1999 | Maguire et al. | |
| 6,033,399 A | 3/2000 | Gines | |
| 6,063,078 A | 5/2000 | Wittkampf | |
| 6,071,281 A | 6/2000 | Burnside et al. | |
| 6,092,528 A | 7/2000 | Edwards | |
| 6,104,954 A | 8/2000 | Blunsden | |
| 6,123,702 A | 9/2000 | Swanson et al. | |
| 6,183,468 B1 | 2/2001 | Swanson et al. | |
| 6,245,065 B1 | 6/2001 | Panescu et al. | |
| 6,264,653 B1 | 7/2001 | Falwell | |
| 6,283,987 B1 | 9/2001 | Laird et al. | |
| 6,346,104 B2 | 2/2002 | Daly et al. | |
| 6,355,031 B1 | 3/2002 | Edwards et al. | |
| 6,411,852 B1 | 6/2002 | Danek et al. | |
| 6,423,057 B1* | 7/2002 | He .................... | A61B 18/1206 606/34 |
| 6,458,121 B1 | 10/2002 | Rosenstock et al. | |
| 6,488,679 B1 | 12/2002 | Swanson et al. | |
| 6,494,880 B1 | 12/2002 | Swanson et al. | |
| 6,558,378 B2 | 5/2003 | Sherman et al. | |
| 6,575,969 B1 | 6/2003 | Rittman, III et al. | |
| 6,634,363 B1 | 10/2003 | Danek et al. | |
| 6,635,056 B2 | 10/2003 | Kadhiresan et al. | |
| 6,640,119 B1* | 10/2003 | Budd .................... | A61B 5/0538 600/374 |
| 6,733,498 B2 | 5/2004 | Paton et al. | |
| 6,939,346 B2 | 9/2005 | Kannenberg et al. | |
| 7,027,869 B2 | 4/2006 | Danek et al. | |
| 7,104,987 B2 | 9/2006 | Biggs et al. | |
| 7,131,445 B2 | 11/2006 | Amoah | |
| 7,160,296 B2 | 1/2007 | Pearson et al. | |
| 7,367,972 B2 | 5/2008 | Francischelli et al. | |
| 2003/0050631 A1 | 3/2003 | Mody et al. | |
| 2003/0069570 A1 | 4/2003 | Witzel et al. | |
| 2003/0093069 A1* | 5/2003 | Panescu ................ | A61N 1/056 606/34 |
| 2003/0130711 A1* | 7/2003 | Pearson ............ | A61B 18/1477 607/101 |
| 2003/0153905 A1* | 8/2003 | Edwards ............ | A61B 18/1492 606/41 |
| 2003/0187430 A1 | 10/2003 | Vorisek | |
| 2003/0199863 A1 | 10/2003 | Swanson et al. | |
| 2003/0236455 A1 | 12/2003 | Swanson et al. | |
| 2004/0015162 A1 | 1/2004 | McGaffigan | |
| 2004/0031494 A1* | 2/2004 | Danek .................. | A61B 18/1492 128/898 |
| 2004/0153056 A1 | 8/2004 | Muller et al. | |
| 2005/0010270 A1 | 1/2005 | Laufer | |
| 2005/0096644 A1 | 5/2005 | Hall et al. | |
| 2005/0101948 A1 | 5/2005 | Harano et al. | |
| 2005/0137662 A1 | 6/2005 | Morris et al. | |
| 2005/0177210 A1 | 8/2005 | Leung et al. | |
| 2005/0193279 A1 | 9/2005 | Daners | |
| 2005/0251128 A1 | 11/2005 | Amoah | |
| 2006/0079887 A1 | 4/2006 | Buysse et al. | |
| 2006/0106375 A1* | 5/2006 | Werneth ............ | A61B 18/1492 606/32 |
| 2006/0142801 A1 | 6/2006 | Demarais et al. | |
| 2006/0247726 A1 | 11/2006 | Biggs et al. | |
| 2006/0247727 A1 | 11/2006 | Biggs et al. | |
| 2006/0247746 A1* | 11/2006 | Danek .................... | A61N 1/403 607/115 |
| 2007/0074719 A1 | 4/2007 | Danek et al. | |
| 2007/0106292 A1 | 5/2007 | Kaplan et al. | |
| 2007/0118184 A1 | 5/2007 | Danek et al. | |
| 2008/0097424 A1 | 4/2008 | Wizeman et al. | |
| 2008/0103407 A1 | 5/2008 | Bolea et al. | |

FOREIGN PATENT DOCUMENTS

| | | |
|---|---|---|
| JP | 2001037776 A | 2/2001 |
| WO | WO-9424949 A1 | 11/1994 |
| WO | WO-1999003413 A1 | 1/1999 |
| WO | WO-2006078863 A2 | 7/2006 |

OTHER PUBLICATIONS

Cantwell C. P., et al., "Radiofrequency Ablation of Bone with Cooled Probes and Impedance Control Energy Delivery in a Pig Model: MR Imaging Features," Journal of Vascular and Interventional Radiology, 2007, vol. 18 (8), pp. 1011-1020.

Co-pending U.S. Appl. No. 11/777,225, filed Jul. 12, 2007.

Goldberg S. N., et al., "Percutaneous Radiofrequency Tissue Ablation: Optimization of Pulsed-Radiofrequency Technique to Increase Coagulation Necrosis," Journal of Vascular and Interventional Radiology, 1999, vol. 10 (7), pp. 907-916.

International Search Report and Written Opinion dated Nov. 7, 2008 for International Application No. PCT/US2008/071037, 7 pages.

Lee J. M., et al., "Radiofrequency Thermal Ablation in Canine Femur: Evaluation of Coagulation Necrosis Reproducibility and MRI-Histopathologic Correlation," American Journal of Roentgenology, 2005, vol. 185 (3), pp. 661-667.

Strickberger S. A., et al., "Relation between Impedance and Temperature during Radiofrequency Ablation of Accessory Pathways," American Heart Journal, 1995, vol. 130 (5), pp. 1026-1030.

Thiagalingam A., et al., "Impedance and Temperature Monitoring Improve the Safety of Closed-Loop Irrigated-Tip Radiofrequency Ablation," Journal of Cardiovascular Electrophysiology, 2007, vol. 18 (3), pp. 318-325.

* cited by examiner

SYSTEM AND METHOD FOR CONTROLLING POWER BASED ON IMPEDANCE DETECTION, SUCH AS CONTROLLING POWER TO TISSUE TREATMENT DEVICES

CROSS-REFERENCE TO RELATED APPLICATIONS

This application is a continuation of U.S. application Ser. No. 14/799,346, filed on Jul. 14, 2015, now U.S. Pat. No. 10,278,765, which is a continuation of U.S. application Ser. No. 12/179,301, filed on Jul. 24, 2008, now U.S. Pat. No. 9,108,052, which claims the benefit of priority under 35 USC § 119(e) to U.S. Provisional Application No. 60/951,655, filed on Jul. 24, 2007, the entireties of each of which are incorporated herein by reference.

TECHNICAL FIELD

The present application relates generally to medical treatment devices, such as devices that treat lung diseases by applying energy to airways to reduce the resistance to airflow in the airways.

BACKGROUND

Asthma is a disease that makes it difficult to breathe and in many cases can be debilitating. Asthma is generally manifested by (i) bronchoconstriction, (ii) excessive mucus production, and/or (iii) inflammation and swelling of airways that cause widespread but variable airflow obstructions. Asthma can be a chronic disorder often characterized by persistent airway inflammation, but asthma can be further characterized by acute episodes of additional airway narrowing via contraction of hyper-responsive airway smooth muscle tissue.

Conventional pharmacological approaches for managing asthma include: (i) administering anti-inflammatories and long-acting bronchodilators for long-term control, and/or (ii) administering short-acting bronchodilators for management of acute episodes. Both of these pharmacological approaches generally require repeated use of the prescribed drugs at regular intervals throughout long periods of time. However, high doses of corticosteroid anti-inflammatory drugs can have serious side effects that require careful management, and some patients are resistant to steroid treatment even at high doses. As such, effective patient compliance with pharmacologic management and avoiding stimuli that triggers asthma are common barriers to successfully managing asthma.

Asthmatx, Inc. has developed new asthma treatments that involve applying energy to alter properties of the smooth muscle tissue or other tissue (e.g., nerves, mucus glands, epithelium, blood vessels, etc.) of airways in a lung of a patient. Several embodiments of methods and apparatus related to such treatments are disclosed in commonly-assigned U.S. Pat. Nos. 6,411,852, 6,634,363, 7,027,869, and 7,104,987; and U.S. Published Application Nos. US2005/0010270 and US2006/0247746, all of which are incorporated by reference herein in their entirety.

Many embodiments of the foregoing asthma treatments that apply energy to tissue of the airways use catheters that can be passed (e.g., navigated) through the tortuous passageways defined by the lung airways. FIG. 1, for example, illustrates a bronchial tree 90 in which the various bronchioles 92 decrease in size and have many branches 96 as they extend from the right and left bronchi 94. Accordingly, the treatment devices should be configured to treat airways of varying sizes as well as function properly when repeatedly deployed after navigating through the tortuous anatomy.

It is also desirable to control the amount and rate of energy delivered to the treatment site. For example, the energy delivery devices for delivering radio frequency (RF) energy to tissue in the lung airways disclosed in the commonly-assigned patents and applications incorporated by reference above have been controlled by measuring the temperature of one of the electrodes during energy delivery. Other types of treatment devices that deliver RF energy for other applications outside of the lung airways, such as ablation and cauterization devices, have controlled the delivery of energy to cardiac and vasculature tissue based on measuring factors other than temperature. For example, ablation and cauterization devices have monitored impedance during a procedure and terminated energy deliver when a sharp increase in the impedance is measured. This sharp increase may correlate with a desired end result, such as tissue desiccation or protein denaturation. As such, existing ablation and cauterization systems may terminate energy delivery based on a direct relationship between an increase in impedance and an increase in temperature.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the disclosure and are not intended to limit the scope of the disclosure.

DETAILED DESCRIPTION

Overview

Figure 1:
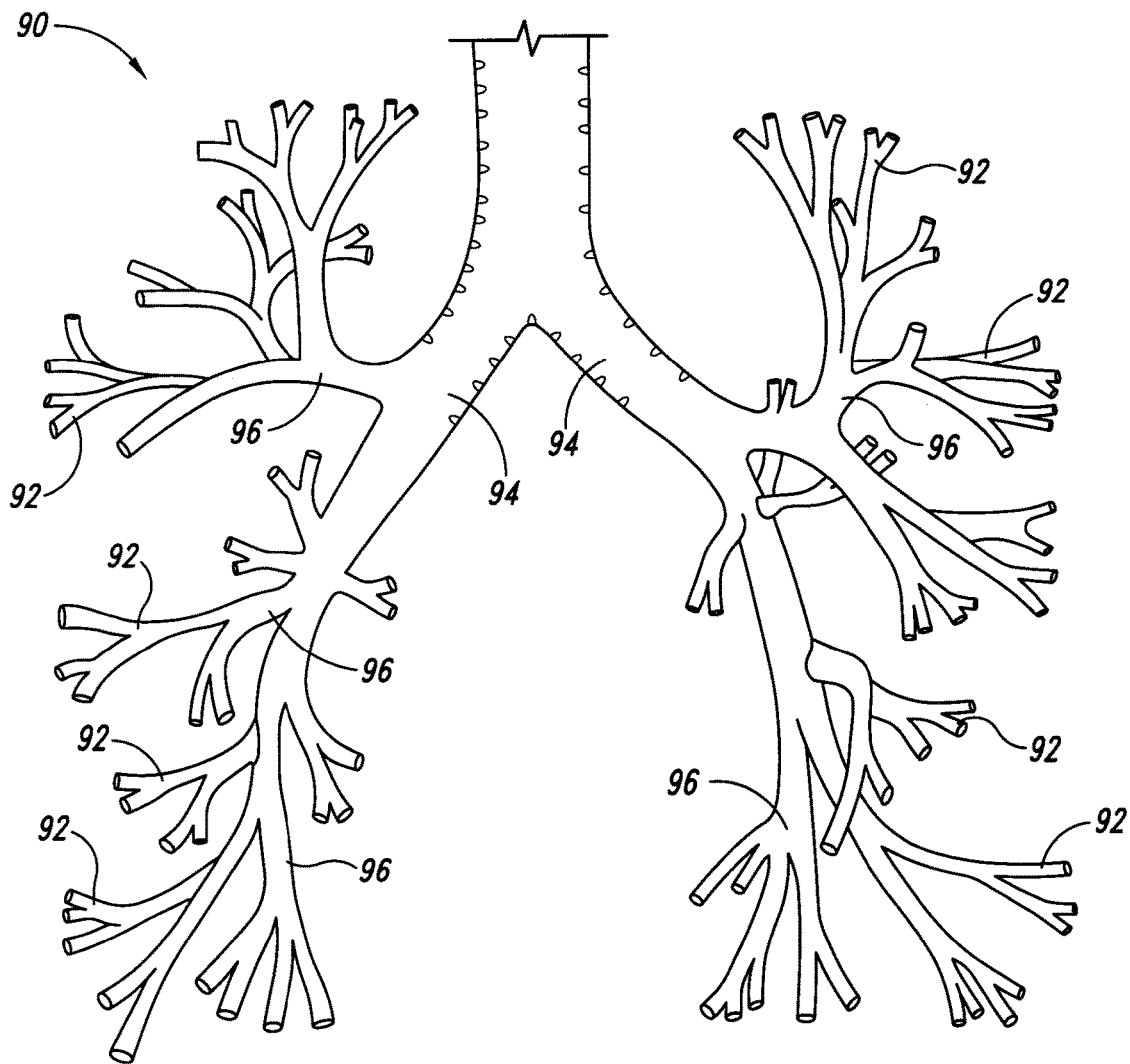
FIG. 1 is an illustration of the airways within a human lung.

Devices, systems, and methods for controlling the treatment of internal tissue using measured impedance of an energy delivery device and/or targeted tissue are described. In some examples, the system controls power to the energy delivery device based on the measured impedance. The system may determine a desired or set impedance level related to parameters of the treatment site and/or of the energy delivery device, measure a current or present impedance level during or prior to energy delivery to the treatment site, and control the power to maintain the temperature or other parameter of the treatment site based on the two impedances.

Several of the details set forth below are provided to describe the following examples and methods in a manner sufficient to enable a person skilled in the relevant art to practice, make and use them. Several of the details and advantages described below, however, may not be necessary to practice certain embodiments and methods of the technology. Additionally, the technology may include other examples and methods that are within the scope of the claims but are not described in detail.

The particular features, structures, routines, steps, or characteristics may be combined in any suitable manner in one or more examples of the technology. The headings provided herein are for convenience only and are not intended to limit or interpret the scope or meaning of the claimed technology.

In some examples, the system provides closed loop power control of energy delivery devices based on impedance feedback. By monitoring impedance at low non-ablative temperatures (e.g., temperatures below tissue desiccation or protein denaturation temperatures), several embodiments of the system may enable the simplification of devices used in the treatment systems and/or may result in more stable or consistent treatment delivery. At short treatment times and/or low power and temperature levels, impedance may inversely correlate to temperature because electrical conductivity of the tissue increases because of increased mobility of charge carriers within the tissue. The impedance accordingly decreases with increases in temperature in such circumstances (impedance=1/conductivity). This inverse correlation of temperature and impedance enables the system to (a) measure the impedance of the system using electrodes of an energy delivery device that provide energy to target tissue in order to receive feedback about the temperature or other parameters of the target tissue, and (b) adjust power to the energy delivery device accordingly.

In some cases, for example, measuring impedance may eliminate the need to measure temperature during the delivery of radio frequency or other energy to tissue, and thus several embodiments of the system may utilize catheters without thermocouples or other temperature measurement components. As a result, several embodiments of treatment devices may be small, simple, and relatively less expensive to manufacture. Additionally, controlling power by measuring impedance may enable the system to more accurately or holistically assess the state of the tissue around the passageway because measuring impedance may result in less temperature variability in the tissue versus measuring temperature at only a single location in the passageway. This may result in a more accurate treatment and/or in more consistent energy delivery between applications because impedance monitoring may be less susceptible to variation than temperature monitoring within a treatment location or between treatment locations.

Embodiments of a Treatment System

Specific details of several embodiments of treatment systems and methods for delivering energy to passageways in a patient are described. Although many of the embodiments are described below with respect to delivering RF energy to airways in a lung of a patient to treat asthma, other embodiments that deliver other energy modalities to lung airways or other types of passageways or tissues (e.g., blood vessel, skin, etc.) for treating other indications may be within the scope of the invention. For example, other types of energy modalities can include thermal (resistive and/or infrared), microwave, laser, ultrasonic (e.g., HIFU), cryoablation, radiation, or other modalities. Moreover, several other embodiments of the invention can have different configurations, components, or procedures than those described in this section.

Figure 2A:
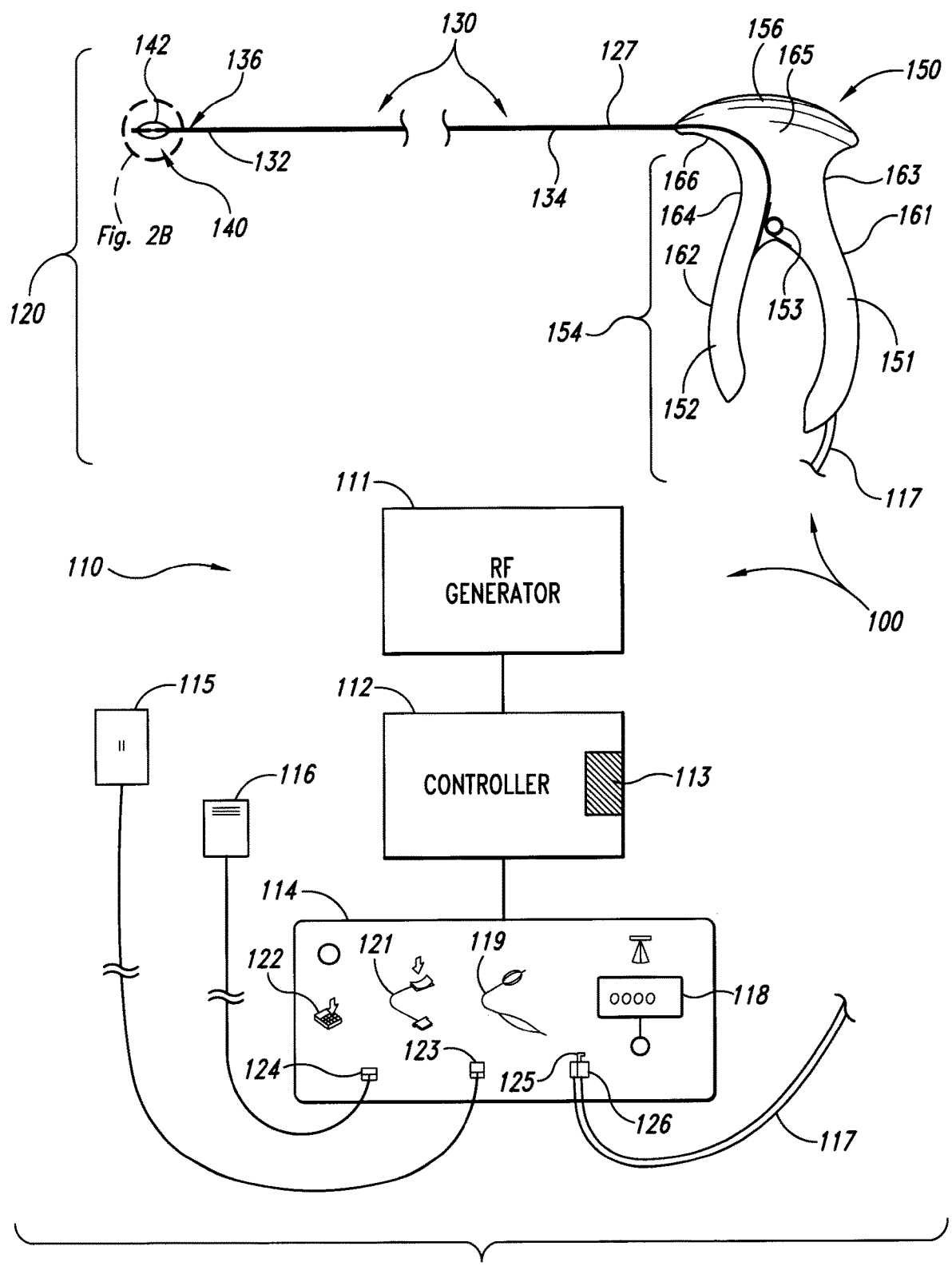
FIG. 2A is a schematic view illustrating a system for delivery of energy according to some embodiments.

FIG. 2A is a schematic view illustrating a system 100 for delivering energy to passageways in a patient having a power/control unit 110 and an energy delivery device 120 in accordance with an embodiment of the disclosure. The power/control unit 110 can include an energy generator 111 (e.g., power supply), a controller 112 having a processor 113, and a user interface 114. The energy generator 111 and controller 112 can provide RF energy to the energy delivery device 120, but in other embodiments the energy generator 111 and controller 112 can provide other energy modalities. The controller 112 can contain safety algorithms and other control algorithms that control (i) the power output to the energy delivery device 120 and (ii) the indicators 118, 119, 121, 122 of the user interface 114. The power/control unit 110 can further include one or more connections 123, 124, 125 for an optional return electrode 115 for monopolar RF configurations, an optional switch 116 (e.g., an actuation pedal) for directing the controller 112 to cause the energy generator 111 to provide energy, and a conductive line 117 and connector 126 coupled to the energy delivery device 120. It will be appreciated that the depictions herein are for illustrative purposes only and do not necessarily reflect the actual shape, size, or dimensions of the system or device.

The energy delivery device 120 is an example of a treatment device for treating asthma or other indications associated with passageways in a human. The embodiment of the energy delivery device 120 illustrated in FIG. 2A includes an elongated body 130 with a distal portion 132 and a proximal portion 134, an energy delivery unit 140 at the distal portion 132, and a handle 150 at the proximal portion 134. The length of the elongated body 130 should be sufficient to access the target tissue in airways of the lung or other passageways targeted for treatment. For example, the length of the elongated body 130 can be from approximately 0.5-8 feet to allow passage through a bronchoscope and reach targeted airways deep within the lungs. The elongated body 130 can also be configured to treat airways as small as 3 mm in diameter, but the elongated body 130 is not limited to treating airways of any particular size such that airways smaller or larger than 3 mm may be treated. Typically, the delivery unit 140 expands/contracts to variable sizes to treat airways between 3-10 mm.

Several embodiments of the elongated body 130 are flexible catheters configured to slide through the working lumen of an access device (e.g., bronchoscope). The elongated body 130 can also include a plurality of markers 136 at the distal section 132 to position the energy delivery unit 140 relative to an access device (not shown in FIG. 2A) and a proximal marker(s) 127 so as to assist in expedient positioning of the energy delivery unit 140 out of the distal end of the access device. Specific embodiments of elongated bodies with markers suitable for use in the system 100 are described in U.S. patent application Ser. No. 11/777,225 and in U.S. patent application Ser. No. 11/551,639 and in U.S. Published Application No. US2007/0106292A1, all of which are incorporated herein by reference in their entirety.

Figure 2B:
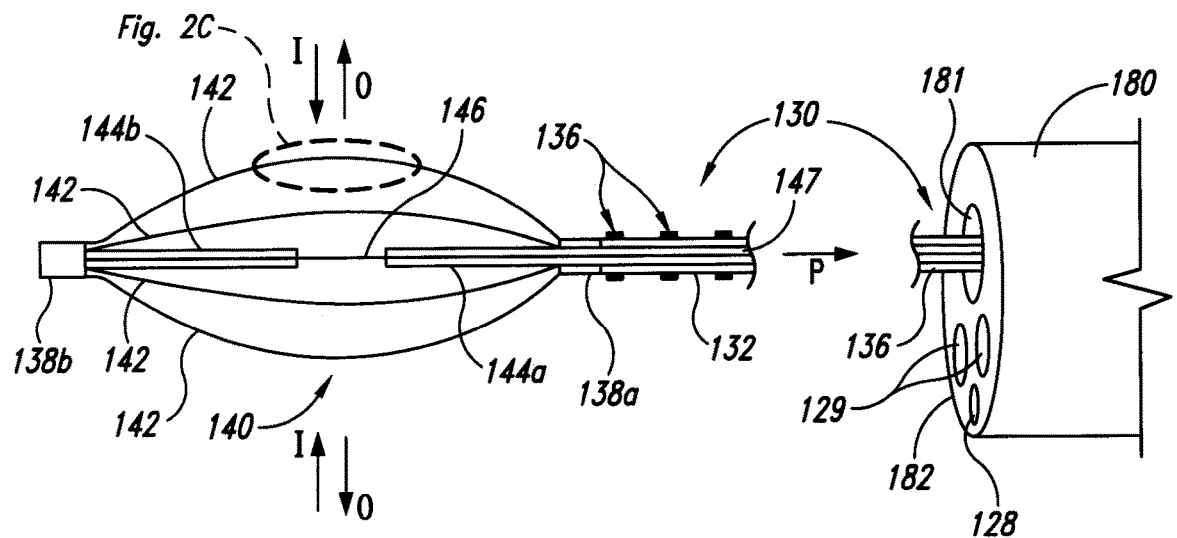
FIGS. 2B and 2C are side views in partial cross-section illustrating a portion of a treatment device for supplying energy to tissue within the body.

The energy delivery unit 140 can have at least one energy delivery element, such as an electrode 142, configured to deliver energy to the tissue of an airway or other passageway in the patient. FIG. 2B is a partial cross-sectional view showing an embodiment of the energy delivery unit 140 in greater detail. In this embodiment, the energy delivery unit 140 includes four electrodes 142, a proximal sleeve 138*a* and a proximal alignment extrusion or retainer 144*a* fixed to the elongated body 130 and attached to the proximal ends of the electrodes 142, and a distal sleeve 138*b* and a distal alignment extrusion or retainer 144*b* attached to the distal ends of the electrodes 142. The energy delivery device 120 can also include a wire 146 attached to the distal retainer 144*b* at the distal sleeve 138*b* and configured to move through a lumen 147 of the elongated body 130 and the proximal retainer 144*a*.

The example of the energy delivery unit 140 illustrated in FIG. 2B is a "basket-type" configuration in which the electrodes 142 move outwardly (arrows O) as the wire 146 moves proximally (arrow P) relative to the elongated body 130. The electrodes 142 can move inwardly (arrows I) by releasing the wire 146 such that a spring or other resilient element in the handle 150, and/or the spring force of the electrodes 142, drives the wire 146 distally. The outward/inward movement of the electrodes 142 is useful when the device is operated intraluminally or in airways in the lungs because the energy delivery unit 140 can be advanced through a working lumen 181 of an access device 180 while the electrodes 142 are in a low-profile configuration, and then the electrodes 142 can repeatedly be moved outwardly according to the varying sizes of the passageways. Visualization of this may be facilitated by an imaging lumen 128 and/or light optical fiber lumens 129 of the access device 180 (or optical chip(s) or fiber(s) mounted at the distal end of the access device). In this illustration, the pull wire 146 may also comprise a conductive wire between the electrodes 142 and the energy supply 111.

Figure 2C:
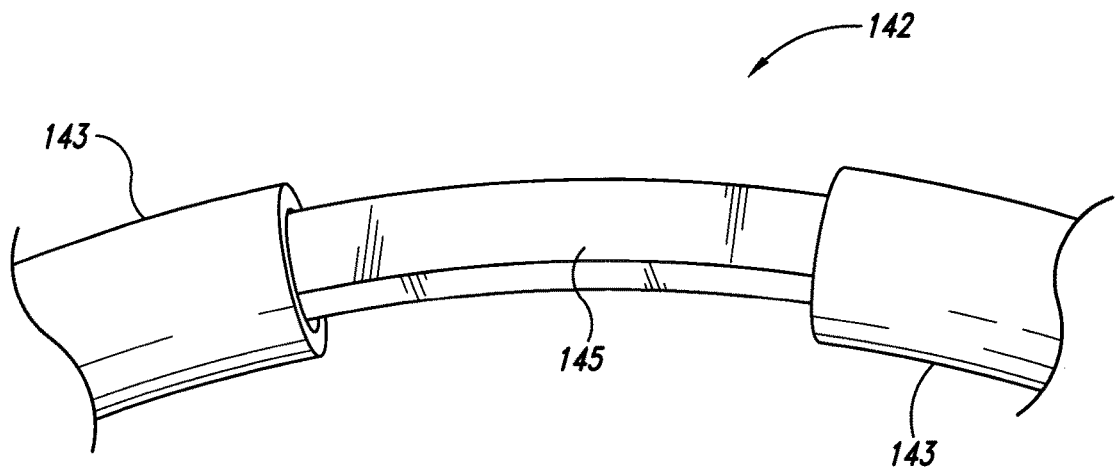

FIG. 2C is an exploded view illustrating a portion of one electrode 142 in greater detail. The electrode 142 has an outer insulating material or coating 143 at proximal and distal ends so as to define a non-insulated, active central portion 145 of the electrode 142 which delivers controlled energy to the tissue walls. Specific embodiments of suitable electrode configurations are disclosed in U.S. Publication No. US2007/0118184, which is incorporated herein by reference in its entirety. Further embodiments of suitable electrodes and retainers for preventing electrode inversions and limiting basket expansions are disclosed in U.S. Publication No. US2007/0106292. The system 100 may deliver energy to target sites via the energy delivery device 120 in a variety of treatment patterns. Further details with respect to other designs and types of treatment devices, examples of energy, and/or examples of treatment patterns may be found in commonly-assigned U.S. Pat. No. 6,411,852.

Referring back to FIG. 2A, the illustrated example of the handle 150 is configured so that a single operator can hold an access device (e.g., a bronchoscope) in one hand (e.g., a first hand) and use the other hand (e.g., a second hand) to (i) advance the elongated body 130 through a working lumen of the access device until the energy delivery unit 140 projects beyond the distal end of the access device and is positioned at a desired target site and (ii) pull the wire 146 (FIG. 2B) to move the electrodes 142 outwardly until they contact the sidewall of an airway passage while the catheter is held in place relative to the access device with the same second hand. The same operator can also operate the switch 116 of the power/control unit 110 such that the entire procedure can be performed by a single person.

In one embodiment, the handle 150 has a first portion 151 and a second portion 152 rotatably coupled to the first portion 151 by a joint 153. The first portion 151 and/or the second portion 152 are one example of an actuator for manipulating the electrodes 142. The first and second portions 151-152 can be configured to form a grip 154 and a head 156 located at an upper portion of the grip 154. The head 156, for example, can project outwardly from the grip such that a portion of the grip 154 is narrower than the head 156. In the specific embodiment illustrated in FIG. 2A, the first portion 151 has a first curved surface 161 with a first neck portion 163 and a first collar portion 165, and the second portion 152 has a second curved surface 162 with a second neck portion 164 and a second collar portion 166. The first and second curved surfaces 161-162 can be configured such that they are arranged to define a hyperbolic-like shaped grip when viewed from a side elevation.

In several embodiments of the system, the controller 112 includes a processor that is generally configured to accept information from the system 100 and system components, and process the information according to various algorithms to produce control signals for controlling the energy generator. The processor may also accept information from the system and system components, process the information according to various algorithms, and produce information signals. The information signals may be directed to the visual indicators, a digital display or an audio tone generator of the user interface to inform the user of the system status, component status, procedure status, or any other useful information that is being monitored by the system. The processor of the controller 112 may be a digital IC processor, analog processor or any other suitable logic or control system that carries out the control algorithms.

Several embodiments of the system 100 shown in FIGS. 2A and 2B can be controlled by measuring the impedance before, during and/or after delivering energy to the tissue of the passages. The following discussion provides a brief, general description of a suitable environment in which the control of the system 100 may be implemented. Although not required, aspects of the system and various components (such as the controller 112) are described in the general context of computer-executable instructions, such as routines executed by a general-purpose computer (e.g., personal computer, laptop, mobile device, hand-held computer, etc.). Those skilled in the relevant art will appreciate that the system may be practiced with other communications, data processing, or computer system configurations, including Internet appliances, other handheld devices (including personal digital assistants (PDAs)), embedded computers, multi-processor systems, microprocessor-based or programmable consumer electronics, network PCs, mini-computers, mainframe computers, and the like. The terms "computer" and the like are generally used interchangeably and refer to any of the above devices and systems, as well as any data processor. For example, an exemplary computing system may include a processor, input devices, data storage devices, such as hard disks or removable media, display devices, and/or output devices. Additionally, the system 100 may connect to various networked environments via a network connection or a wireless transceiver.

Aspects of the system may be embodied in a special purpose computer or data processor that is specifically programmed, configured, or constructed to perform one or more of the computer-executable instructions explained in detail herein. Aspects of the system may also be practiced in distributed computing environments where tasks or modules are performed by remote processing devices, which are linked through a communication network. In a distributed computing environment, program modules may be located in both local and remote memory storage devices.

Aspects of the system may be stored or distributed on computer-readable media, including magnetically or optically readable computer disks, as microcode on semiconductor memory, nanotechnology memory, organic or optical memory, or other portable data storage media. Indeed, computer-implemented instructions, data structures, screen displays, and other data under aspects of the system may be distributed over the Internet or over other networks (including wireless networks), on a propagated signal on a propagation medium (e.g., an electromagnetic wave(s), a sound wave, etc.) over a period of time, or may be provided on any analog or digital network (packet switched, circuit switched, or other scheme). Those skilled in the relevant art will recognize that portions of the technology reside on a server computer, while corresponding portions reside on a client computer.

Monitoring and Controlling Power to the Energy Delivery Device

Several embodiments of the controller 112 perform closed loop control of the energy delivery based on the measurement of impedance of targeted tissue sites. For example, the system may measure the impedance, determine an impedance level that corresponds to a desired temperature, and supply power to an energy delivery device until the impedance level is reached. The system may also supply power to the energy delivery device to maintain a desired level of energy at the target site based on impedance measurements. In several embodiments, the system controls the power output to maintain the impedance at a level that is less than an initial or base level when power is not applied to the electrodes or at time to when power is first applied to a target tissue (e.g., the beginning of the first pulse). The impedance is initially inversely related to the temperature of the tissue before the tissue begins to ablate or cauterize. As such, the impedance initially drops during the initial portion of the treatment cycle and continues to fluctuate inversely relative to the tissue temperature. The controller 112 can accurately adjust the power output based on the impedance measurements to maintain the impedance, and thus the temperature, in a desired non-ablative range.

Figure 3:
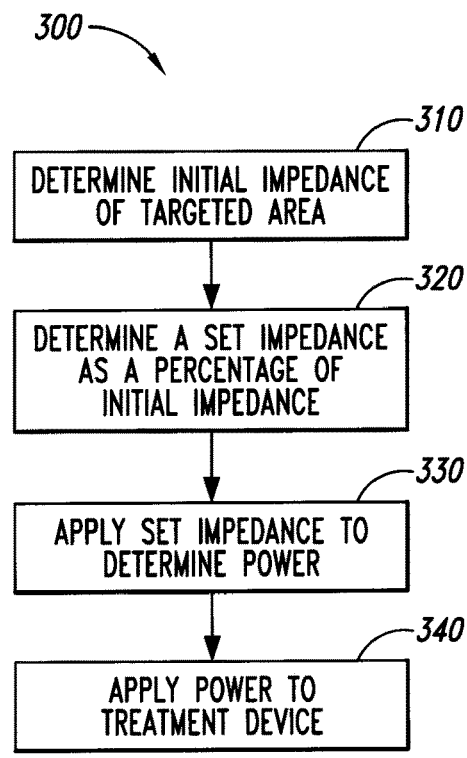
FIG. 3 is a flow diagram illustrating a routine for controlling the power during treatment using impedance measurements.

FIG. 3 illustrates a flow diagram of an embodiment of a routine 300 for controlling the power during treatment based on impedance measurements that includes determining an initial impedance of a targeted area (block 310). For example, the system can determine the initial impedance based on an initial measurement of voltage and current at body temperature of the targeted site or of the energy delivery device. Alternatively, the system may transmit a test or pre-treatment low energy pulse (i.e., that does not heat tissue; non-therapeutic) at the targeted site to determine the initial impedance value.

The routine 300 further includes determining a desired or set impedance that correlates to a desired treatment temperature or temperature range (block 320). In some cases, the system determines the set impedance as a percentage of the initial impedance determined in block 310. Alternatively, the system may determine the set impedance based on parameters of the targeted site (e.g., size of the passageway, initial temperature of the passageway, mucus or moisture content of the passageway, or other physiologic factors), parameters of the energy delivery device (e.g., configuration or geometry of the electrodes, such as expanded, contracted, spacing, length, width, thickness, radius), the desired temperature range, parameters of a test or pre-treatment pulse and/or other parameters associated with the effect of energy on the tissue (e.g., bipolar or monopolar energy delivery). These parameters may be automatically detected from the initial impedance value or may be measured (e.g., a device mounted sensor, a non-contact infrared sensor, or a standard thermometer to measure an initial temperature of the passageway). The routine 300 can also include applying the set impedance to an algorithm, such as a PID algorithm, to determine the power to be applied to an energy delivery device (block 330). Further details with respect to the PID algorithm will be discussed herein.

The routine 300 may also include measuring current or present impedance values during treatment and applying the measured impedance values to the algorithm to control the power needed to achieve, return to, or maintain the desired impedance and/or temperature. For example, during treatment the system may identify a present impedance level as being higher that the set impedance level, and use both the present and set impedance levels as inputs into the PID algorithm to determine the power output to the electrodes. Thus, several embodiments of the system at least periodically monitor the current or present impedance values to deliver the desired amount of energy to the tissue. The routine 300 can then continue by delivering energy to the tissue (block 340) via the energy delivery device in a manner that maintains a desired temperature at the tissue.

In some examples the system may periodically or continuously perform some or all of routine 300. For example, the system may continuously determine the set impedance during a treatment, and adjust power levels based on any changes in the set impedance. The system may periodically determine the set impedance, and may adjust power levels based on a set impedance change being above a certain threshold change. Alternatively, in some examples the system recalculates the set impedance between treatments. For example, after a treatment at a first targeted site, the system may move to a second targeted site, calculate a new set impedance, and adjust the applied power accordingly.

Figure 4:
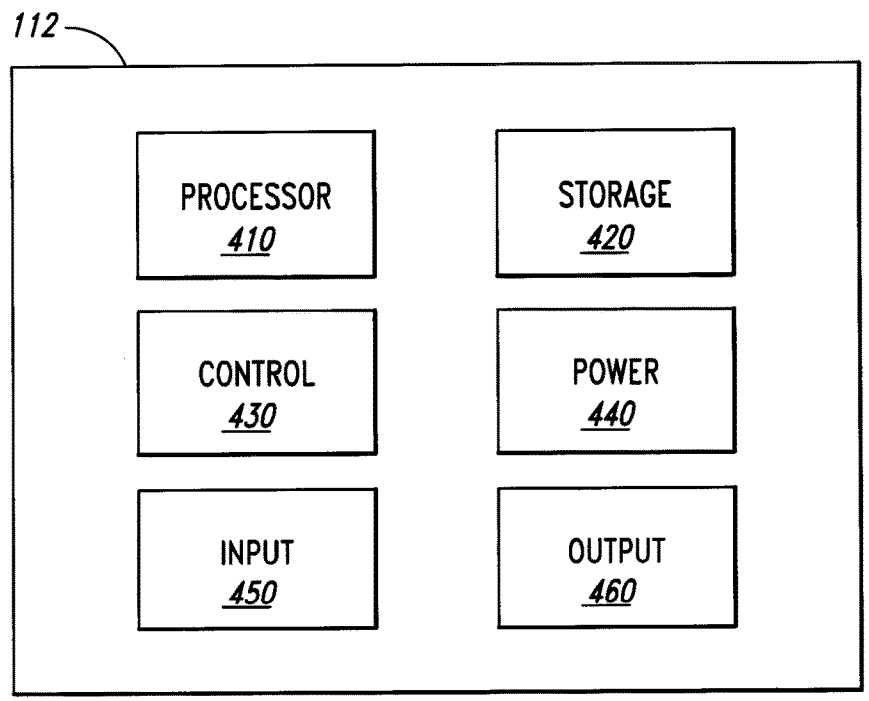
FIG. 4 is a block diagram illustrating a system for controlling the power during treatment using impedance measurements.

FIG. 4 illustrates a block diagram of an embodiment of the controller 112 maintaining the power during treatment based on impedance measurements. The controller 112 includes a processor 410, a storage component 420 such as a memory, a control component 430, a power supply 440, an input component 450, and an output component 460. The control component 430 may contain a routine, algorithm, executable script, or other data structure or program module capable of monitoring impedance and performing actions (e.g., reducing or increasing the power to an energy delivery device) based on reaching or maintaining desired impedance levels, and hence, desired temperature levels. For example, the control component 430 may perform a process of controlling the output of power from an energy source 111 to an energy delivery device. The controller 112 may be configured to deliver energy in either monopolar or bipolar operation.

Calculation of Set Impedance

Figure 5:
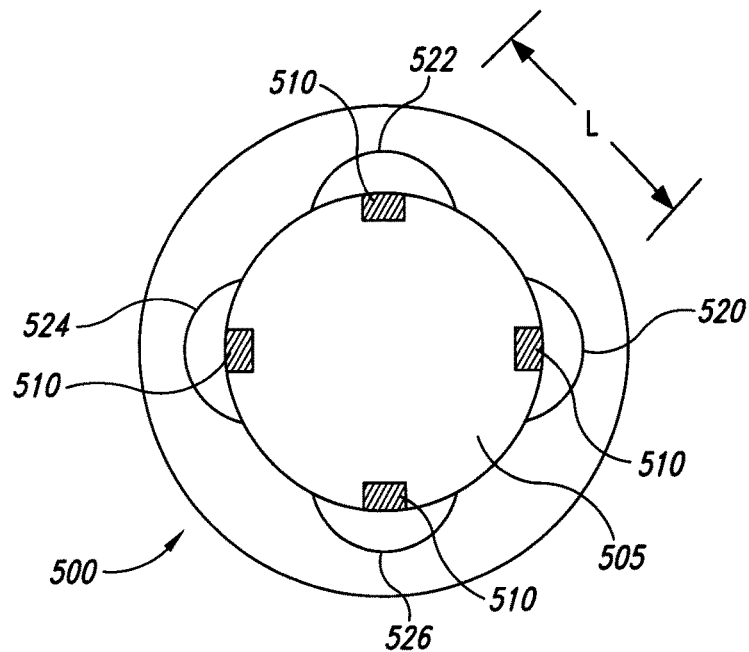
FIG. 5 is a schematic view illustrating an example electrode configuration of a treatment device in a passageway.

As described herein, the system may determine the set impedance using parameters related to a target site, energy delivery device, temperature, or other aspects of the treatment. FIG. 5 schematically illustrates an example of an electrode implementation in an airway 500. The airway 500 has an internal passageway 505, and a plurality of electrodes 510 are spaced around the passageway 505. The electrodes 510 directly affect discrete target sites 520, 522, 524, 526 on the target area around the passageway 505. In this example, the spacing of the electrodes 510 and the size (e.g., diameter) of the passageway 505 determine a length L between the discrete sites, and the length L can influence the set impedance based on the initial impedance. For example, a shorter length L leads to a higher percentage change between the initial impedance and the set impedance because the distance between adjacent heated target sites is small and the heated sites may be a greater factor in determining the set impedance. With larger lengths L the effect of the heated sites on the set impedance may be lesser. Accordingly, a set impedance value may decrease as an airway diameter decreases and increase as an airway diameter increases.

The system may empirically determine the set impedance by modeling the size and/or configuration of the electrodes, the size of the passageway, or other aspects related to the target site or the energy delivery device as described above. Additionally, the system may adjust the set impedance based on measuring a time rate of change of the initial impedance, or may adjust the set impedance based on other factors. For example, the system may determine the set impedance by first determining an initial impedance by measuring the initial impedance when applying minimal energy, and comparing the electrode configuration with the initial impedance to arrive at the set impedance. In some cases, the system may review historical or patient information related to a similar electrode size and/or configuration, and use this information when determining the set impedance.

Alternatively, the system may determine the set impedance based on one or more parameters of a pre-treatment low energy pulse, such as a test pulse. The system may calculate the set impedance ($Z_s$) from one or more parameters of a test pulse, including: (a) the initial pulse impedance ($Z_o$), (b) the average pulse impedance ($Z_{avg}$), (c) the ending pulse impedance ($Z_{end}$), (d) the slope of a pulse impedance curve (the rate of change of the pulse impedance) ($Z_{slope}$), and (e) the pulse energy, and one or more constants ($k_{1-6}$). The test pulse may be in an energy range from about 0.01 to about 1 joule, having a current pulse amplitude in a range from about 0.01 to about 500 milliamps and a pulse duration in a range from about 0.01 to about 500 milliseconds. A constant current pulse is utilized for ease of interpreting impedance changes. For a short duration pulse, the temperature and impedance change at the electrode/tissue interface are proportional to the $I^2R$ heating of adjacent tissue where I is the current amplitude of the pulse and R is the resistance of the adjacent tissue. Pulse amplitude and duration may be set to achieve about a 10% change in impedance from start to end of the test pulse. For example, a typical setting for the test pulse may be 0.5 joules at 100 milliamps for 300 milliseconds, where $Z_s=(k_1*Z_o)+(k_2*Z_{avg})+(k_3*Z_{end})+(k_4*Z_{slope})+k_5$. Values for the one or more constants may be determined by making a straight line fit of test pulse impedance measurements to steady-state impedance using data taken under temperature control. It will be appreciated however that any number of variations of the test pulse parameters may be utilized to determine the set impedance.

Determination of Power Using Set Impedance

Figure 6:
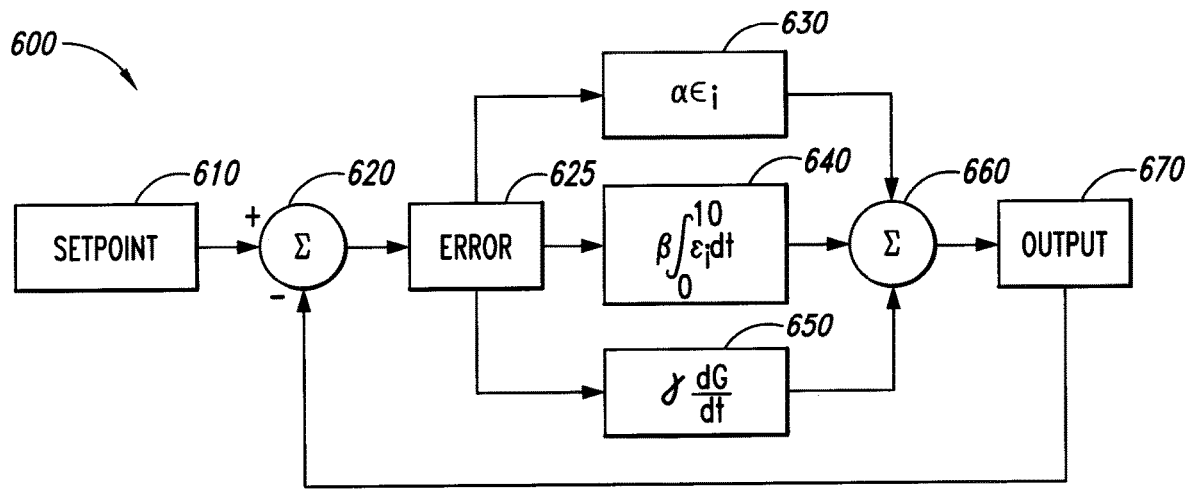
FIG. 6 is a block diagram illustrating an example proportional integral derivative (PID) algorithm for use in calculating applied power.

The system may determine the power to output to an energy delivery device using a PID algorithm, such as an algorithm having one or more variable gain factors. Referring to FIG. 6, a block diagram illustrating an example of a PID algorithm 600 for use in calculating applied power is shown. For example, the control component 430 (FIG. 4) may be a PID controller that receives impedance value(s) as set points 610. The PID controller, can correct for errors between the set point and an output value 670, such as a voltage or current, to apply to an energy delivery device by performing three corrections including: (a) a proportional correction 630 that determines a reaction to current error; (b) an integral correction 640 that determines a reaction based on recent error; and (c) a derivative correction 650 that determines a reaction based on the rate of change of the error. The algorithm sums the three corrections 660 to output the power value 670. Additionally, the system may recalculate using output values using block 620 in order to continuously update and correct for errors. It will be appreciated that a pre-treatment or test pulse, as describe above, may be added to this impedance control algorithm to determine the set impedance.

In this example, the proportional gain (alpha), the integral gain (beta), and derivative gain (gamma) are constants that may be set based on the method involved, the applied temperature, the type of electrodes, parameters of the targeted site, or other factors. The system uses the algorithm 600 to tune the output value to a desired value. For example, the PID controller can overshoot the desired set impedance before reaching the set impedance. Suitable methods for determining the PID coefficients include empirical methods, the Ziegler-Nichols method, the Cohen-Coon method and software implemented models (e.g., finite element analysis).

As described above, several embodiments employ the three parameter controller of FIG. 6. Using a variable gain factor (G) to adaptively control RF energy delivery enables the system to treat a wide range of tissue types including lung tissue bronchus, bronchioles and other airway passages. The variable gain factor scales the coefficients (alpha, beta, and gamma; each a function of the three PID parameters) based on, for example, the temperature response to energy input during the initial temperature ramp up. Examples of PID parameters are presented herein, expressed in alpha-beta-gamma space, for the energy delivering device and/or controller. These settings and timings may be based on testing in various lung tissues using an energy delivering apparatus as described above. In some cases, the system changes the relative weights of alpha, beta, and gamma, depending upon monitored temperature and/or impedance response working in either PID or Alpha-Beta-Gamma coordinate space beyond just scaling the alpha-beta-gamma coefficients with a variable gain factor. This can be done by individually adjusting any or all of the alpha, beta, or gamma constants.

In one example, an error value 625 of the PID algorithm $E_i$ is set to equal the difference in set impedance and current impedance ($Z_s-Z_i$) during treatment. For example, the parameters may be defined by $Z_s=0.9Z_o$, and $E_i=0.9Z_o-Z_i$. Thus, the system may equate the set impedance to be a percentage, generally less than 100% and more typically in a range from about 70% to about 90%, of the initial impedance minus an impedance correction using current impedance. The system may then calculate the current impedance ($Z_i$), in order to provide input into the algorithm. The power can then be found from the value of the Voltage V outputted from the algorithm, as P=IV. In sum, the PID algorithm may be applied to condition the power supply used to control energy used in treatment, among other benefits.

Impedance Correlates to Temperature

As mentioned above, at certain temperatures impedance may be correlated to temperature. For example, at short treatment times (e.g., approximately 10 to 20 seconds or less) and/or low power and temperature levels (e.g., approximately 4 to 40 Watts and approximately 50 to 80 degrees Celsius), impedance may inversely correlate to temperature. As a treatment device heats tissue, electrical conductivity of the tissue increases because of increased mobility of charge carriers within the tissue and impedance decreases (impedance=1/conductivity).

Figure 7:
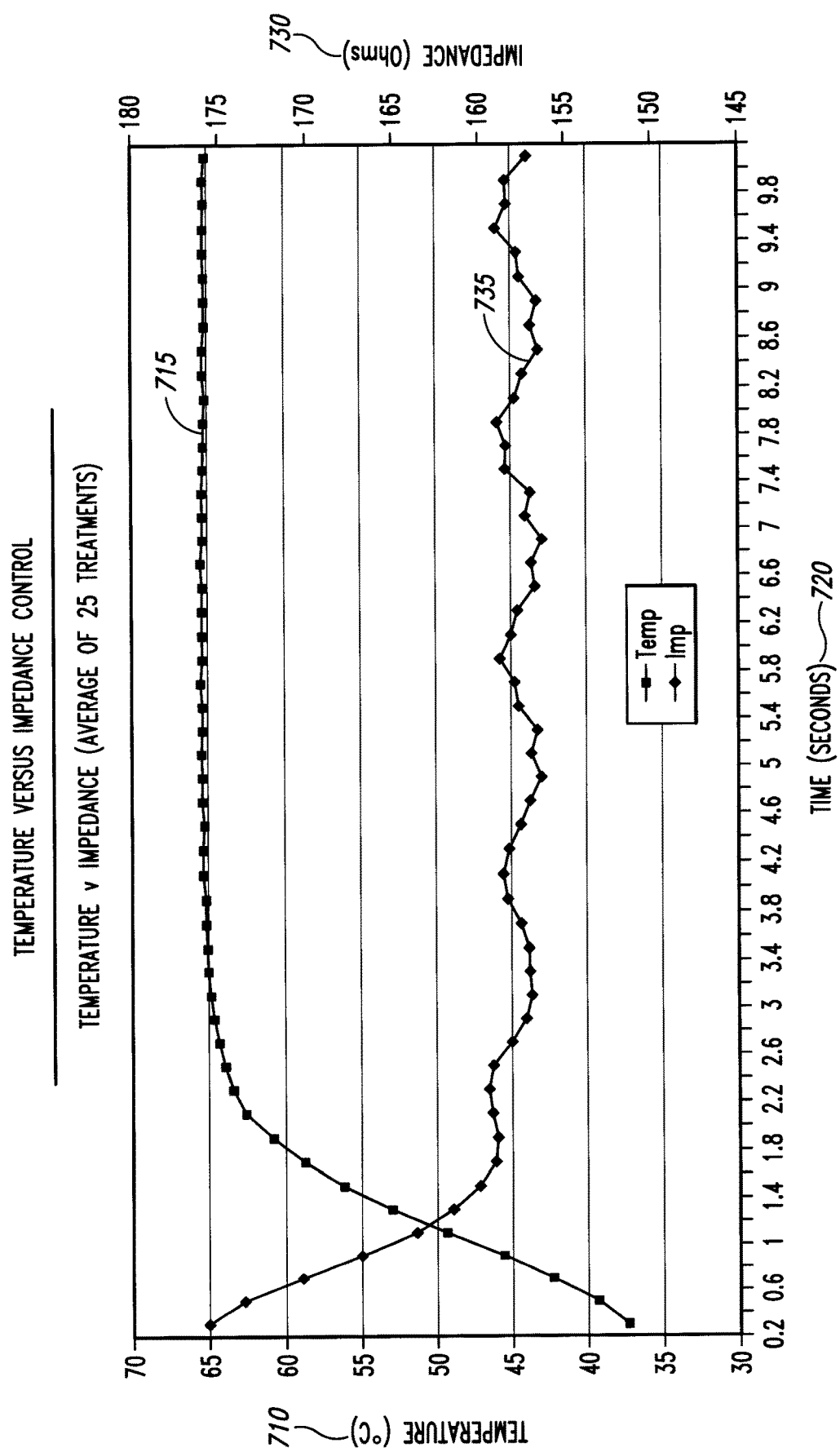
FIG. 7 is a chart illustrating a function of temperature and impedance versus time during treatment.

FIG. 7 is a chart 700 illustrating a function of temperature and impedance versus time during treatment of tissue.

Referring to the Figure, temperature 710 and impedance 730 vary inversely as a function of time 720. As shown at about 1.8-2.0 seconds, the temperature curve 715 begins to show similarities to the impedance curve 735, at about 60-70 degrees (e.g., 65 degrees) Celsius and about 150-160 Ohms. Both curves 715, 735 remain inversely correlated as time increases to 0.10 seconds. Thus, FIG. 7 reflects the correlation of impedance and temperature at low temperatures that enables the system to use impedance measurements to control power levels applied to energy delivery devices in a manner that accurately maintains the temperature of the tissue in a desired range (e.g., a constant treatment tissue temperature in a range from 50 to 80 degrees Celsius).

Figure 8:
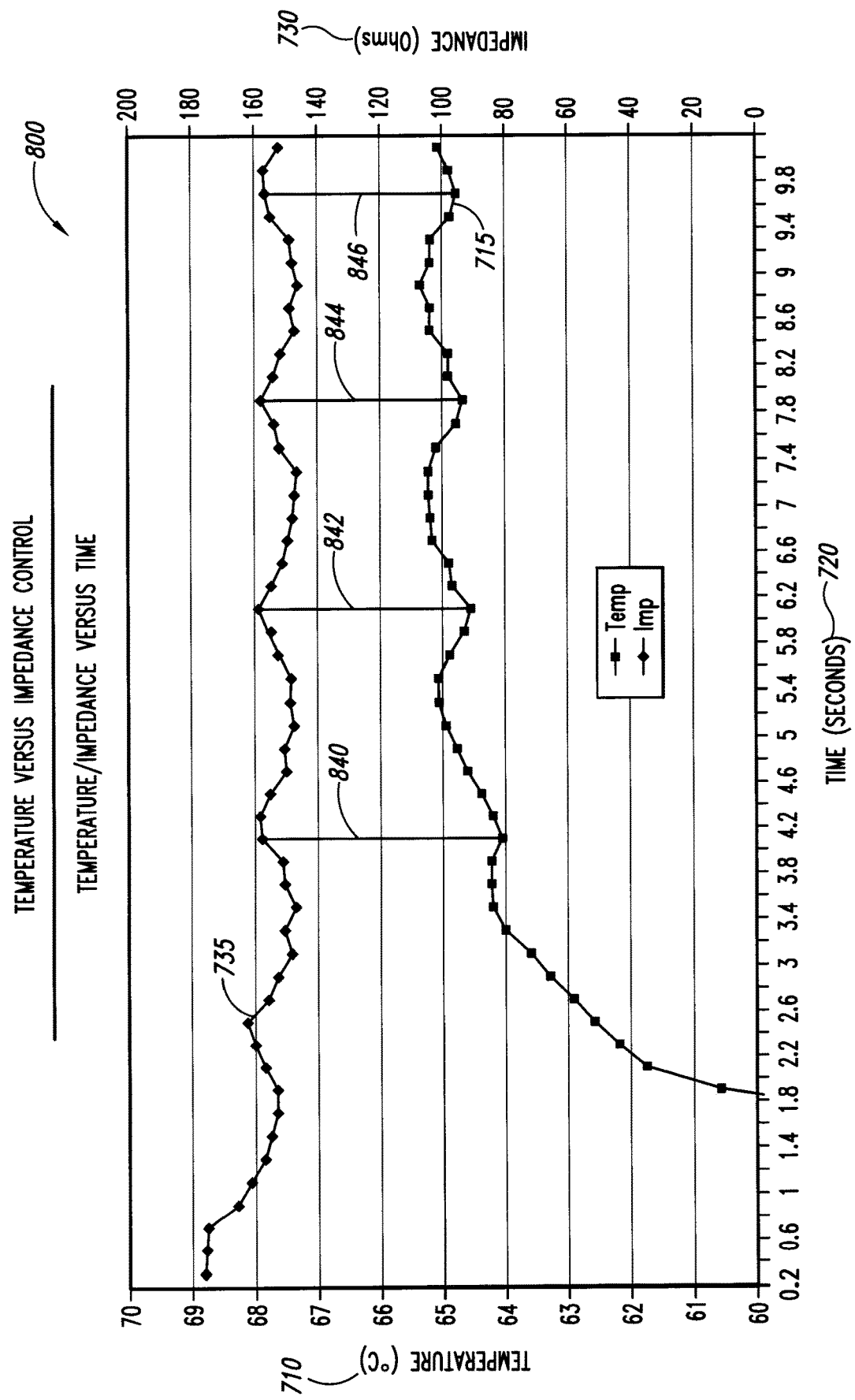
FIG. 8 is a chart further illustrating a correlation between temperature and impedance in more detail.

The chart 800 of FIG. 8 shows the portion of the chart 700 between 1.8 and 9.8 seconds in greater detail. Referring to the varying of temperature 710 and impedance 730 versus time 720 at points 840, 842, 844, and 846, there is a direct and inverse correlation between a peak in impedance and a valley in temperature consistent with how tissue reacts to temperature (at a lower temperature the impedance increases). Thus, FIG. 8 shows a direct and inverse correlation between impedance and temperature.

Controlling power based on impedance enables several embodiments of the system to accurately assess the status of the tissue at several regions around the passageway using a variety of catheter and electrode designs. For example, because the system can measure the impedance directly through the electrodes, it does not need to incorporate a thermocouple or other temperature sensor into a catheter. This may reduce the cost, size, and complexity of the energy delivery device compared to using thermocouples. Additionally, the spacing of electrodes may cause error inducing variations in detected temperature versus the actual temperature of the targeted tissue. For example, measured temperatures at each electrode may vary more than measured impedances. Using impedance, the system is able to reduce these variations and deliver a more stable treatment because impedance values may be averaged across all electrodes (e.g., a weighted average or other non-equal weighting between impedance values).

CONCLUSION

Systems and methods described herein can control the application of energy to tissue using measurements of impedance. The impedance, correlated to the temperature, may be set at a desired level, such as a percentage of initial impedance. The set impedance may be a function of the initial impedance, the size and spacing of the electrodes, the size of a targeted passageway, and other parameters. The set impedance may then be entered into a PID algorithm or other control loop algorithm in order to extract a power to be applied to the energy delivery device.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

The various examples described above can be combined to provide further examples. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the technology may be modified, if necessary, to employ treatment devices with a plurality of treatment units, thermally conductive devices with various configurations, and concepts of the various patents, applications, and publications to provide yet further embodiments of the technology.

These and other changes can be made to the technology in light of the above-detailed description. In general, in the following claims, the terms used should not be construed to limit the technology to the specific examples disclosed in the specification and the claims, but should be construed to include all that operates in accordance with the claims. Accordingly, the technology is not limited by the disclosure, but instead its scope is to be determined entirely by the following claims.

I claim:

1. A method for treating a lumen wall, the method comprising:
    applying energy to the lumen wall, via an energy delivery apparatus including an expandable member movable between a collapsed configuration and an expanded configuration,
        wherein a plurality of energy delivery elements are disposed on the expandable member to cause the lumen wall to reach a temperature from 50° C. to 80° C. for 20 seconds or less;
    delivering a pre-treatment energy pulse to the lumen wall;
    determining at least one initial impedance value using the pre-treatment energy pulse; and
    determining at least one of a plurality of different set impedance values as a function of the at least one initial impedance value,
        wherein an amount of the energy applied by the energy delivery apparatus is based on one of the plurality of different set impedance values correlated to a measured impedance value, and
        wherein each of the different set impedance values corresponds to a different expansion level of the expandable member.

2. The method of claim 1, wherein a lumen defined by the lumen wall is an airway in a lung.

3. The method of claim 2, wherein applying the energy reduces a resistance of the airway to airflow.

4. The method of claim 2, wherein applying the energy damages smooth muscle tissue in the lung.

5. The method of claim 2, wherein applying the energy damages nerve tissue in the lung.

6. The method of claim 2, wherein applying the energy damages epithelial tissue in the lung.

7. The method of claim 1, wherein the different set impedance values increase as the expansion level of the expandable member increases.

8. The method of claim 1, wherein the plurality of different set impedance values are from 70 percent to 90 percent of the at least one initial impedance value.

9. The method of claim 1, further including applying the energy until at least one of the plurality of different set impedance values is reached.

10. A method for treating a lung, the method comprising based on an impedance value, applying energy to an airway wall in the lung, via an energy delivery apparatus including an expandable member movable between a collapsed configuration and an expanded configuration, to reduce a resistance of an airway defined by the airway wall to airflow, without measuring a temperature of the airway wall,
  wherein a plurality of energy delivery elements are disposed on the expandable member,
delivering a pre-treatment energy pulse to the airway wall;
determining at least one initial impedance value using the pre-treatment energy pulse; and
determining at least one of a plurality of different set impedance values as a function of the at least one initial impedance value,
  wherein an amount of the energy applied by the energy delivery apparatus is based on one of the plurality of different set impedance values correlated to a measured impedance value, and
  wherein each of the different set impedance values corresponds to a different expansion level of the expandable member.

11. The method of claim 10, wherein the plurality of different set impedance values are from 70 percent to 90 percent of the at least one initial impedance value.

12. A method for treating a lung, the method comprising:
simultaneously applying therapeutic radiofrequency energy to circumferentially spaced apart treatment sites of an airway wall, via an energy delivery apparatus including an expandable member movable between a collapsed configuration and an expanded configuration, to damage tissue at each of the treatment sites, without measuring a temperature of the airway wall,
  wherein a plurality of energy delivery elements are disposed on the expandable member,
delivering a pre-treatment energy pulse to the airway wall;
determining at least one initial impedance value using the pre-treatment energy pulse; and
determining at least one of the plurality of different set impedance values as a function of the at least one initial impedance value,
  wherein an amount of the radiofrequency energy applied by the energy delivery apparatus is based on one of the plurality of different set impedance values, and
  wherein each of the different set impedance values corresponds to a different expansion level of the expandable member.

13. The method of claim 12, wherein the plurality of different set impedance values are from 70 percent to 90 percent of the at least one initial impedance value.

* * * * *